United States Patent [19]

Amos et al.

[11] 4,442,218

[45] Apr. 10, 1984

[54] METHOD OF MEASURING DEGREE OF PARTITIONING

[75] Inventors: Lynn G. Amos, Painted Post, N.Y.; Charles H. Rogers, Duxbury, Mass.

[73] Assignee: Corning Glass Works, Corning, N.Y.

[21] Appl. No.: 267,580

[22] Filed: May 27, 1981

[51] Int. Cl.³ .................... G01N 33/58; G01N 33/60; G01T 1/00

[52] U.S. Cl. .................... 436/525; 436/527; 436/804; 436/807; 436/823; 436/824; 436/537; 436/500

[58] Field of Search .................... 424/1, 12; 23/230 B; 436/500, 525, 527, 537, 804, 807, 823, 824

[56] References Cited

U.S. PATENT DOCUMENTS

| | | | |
|---|---|---|---|
| 3,853,987 | 12/1974 | Dreyer | 424/1 |
| 3,867,518 | 2/1975 | Coffey et al. | 424/1 |
| 3,886,080 | 5/1975 | Schucker et al. | 252/176 |
| 3,918,909 | 11/1975 | Arlman | 215/6 X |
| 3,961,894 | 6/1976 | Gordon et al. | 424/1.5 X |
| 3,996,345 | 12/1976 | Ullman et al. | 424/12 |
| 4,015,939 | 4/1977 | Lewin et al. | 23/230 B |
| 4,039,652 | 8/1977 | Adams et al. | 424/1.5 X |
| 4,135,880 | 1/1979 | Mangiardi et al. | 23/230 B |
| 4,244,694 | 1/1981 | Farina et al. | 424/1 X |
| 4,272,510 | 1/1981 | Smith et al. | 424/1 X |
| 4,280,816 | 7/1981 | Elahi | 424/1 X |
| 4,297,337 | 10/1981 | Mansfield et al. | 424/1 |
| 4,338,094 | 7/1982 | Elahi | 424/1 X |
| 4,394,391 | 7/1983 | Thorell | 424/366 |

FOREIGN PATENT DOCUMENTS

2018424 10/1979 United Kingdom .
2018986 10/1979 United Kingdom .
2019562 10/1979 United Kingdom .

OTHER PUBLICATIONS

Thorell, *Journal of Nuclear Medicine,* 18, 623, (1977).
LaFontaine et al., Abstract, Third Conference on Diagnostic Immunology, New England College, Henniker, New Hampshire, 16–21, Aug. 1981.
Thorell, *Clin. Chem.,* 27, 1969, (1981).
A. Zettner, *Clin. Chem.,* 19, 699, (1973).
A. Zettner and P. E. Duly, *Clin. Chem.,* 20, 5, (1974).
S. L. Sharpe et al., *Clin. Chem.,* 22, 733, (1976).
Mattiasson et al., J. Immunol. Meth., 38:217–223, (1980).
Cook et al., Clin. Chim. Acta, 47:183–189, (1973).

*Primary Examiner*—Christine M. Nucker
*Attorney, Agent, or Firm*—W. E. Maycock; C. S. Janes, Jr.

[57] ABSTRACT

A method of measuring the degree of partitioning of a labeled species between free and bound states which involves the use of an insoluble porous monolith having a means for binding a portion of the labeled species within the pores thereof, which monolith is capable of substantially attenuating the signal emitted by labeled species subsequently bound within the pores thereof.

16 Claims, 12 Drawing Figures

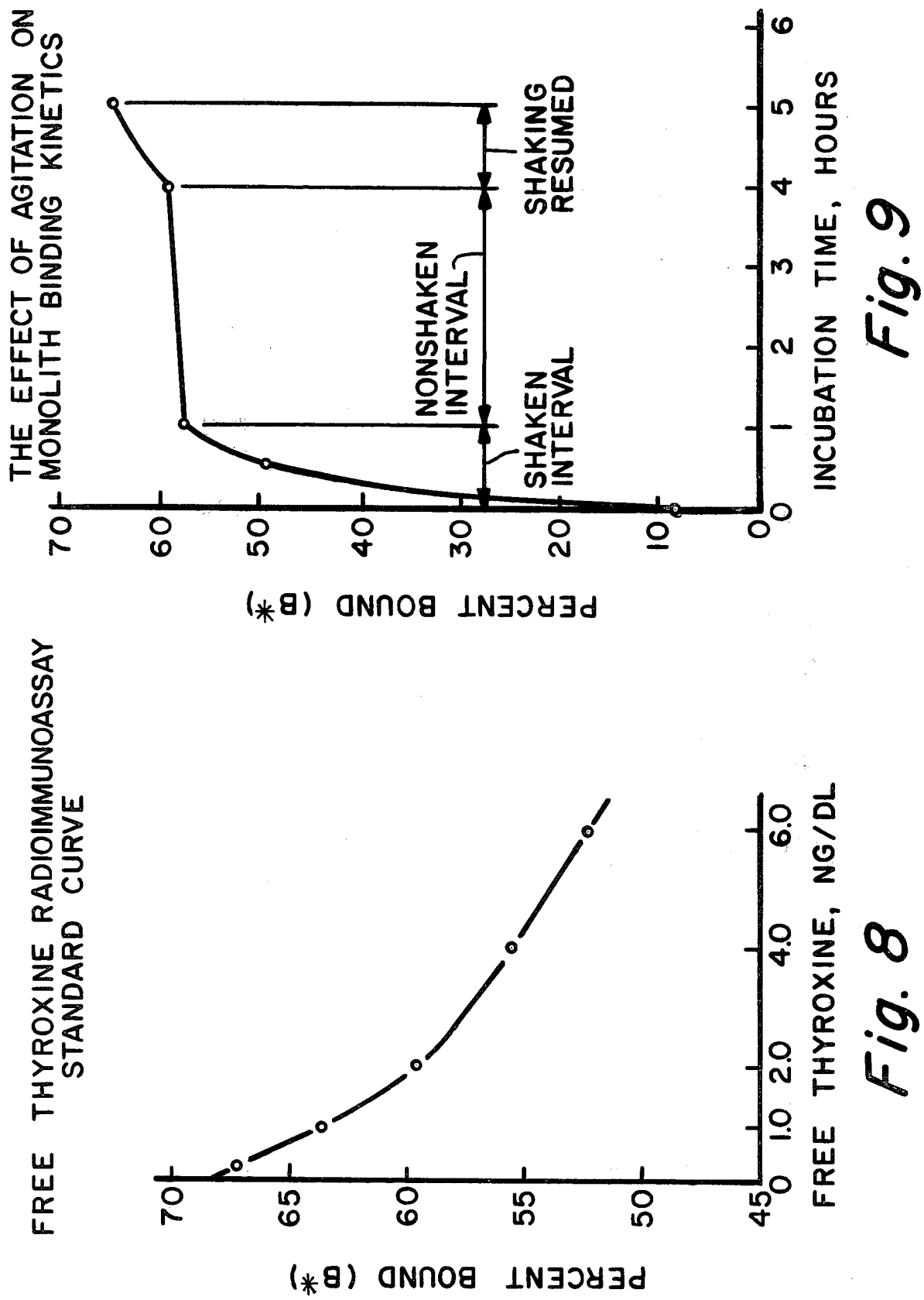

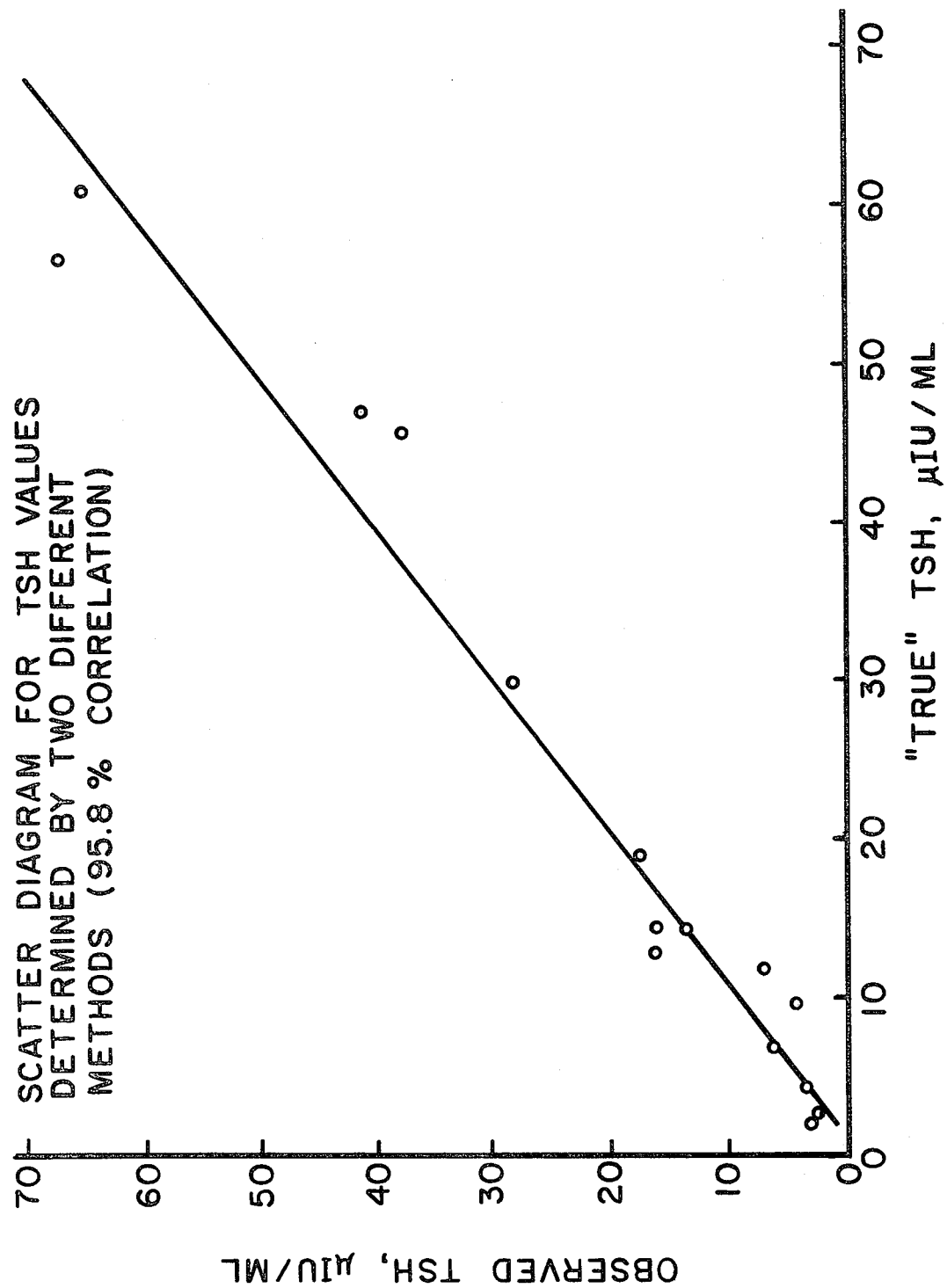

METHOD OF MEASURING DEGREE OF PARTITIONING

BACKGROUND OF THE INVENTION

The present invention relates to a method of measuring the degree of partitioning of a labeled species between free and bound states. The method of the present invention is especially well suited for use in competitive binding assays, such as radioimmunoassays.

In general, the method of the present invention relates to any procedure for determining the quantity or concentration of a particular material present in a liquid medium in which a labeled species is introduced into the liquid medium and subsequently is partitioned between free and bound states. As a practical matter, however, such a procedure usually is a clinical assay for minute quantities of a physiologically-or medically-significant substance in a body fluid such as blood serum or plasma. For a convenience, therefore, the discussion which follows will be limited to such clinical assays. Such discussion, however, is not to be construed as limiting either the spirit or the scope of the present invention.

Clinical assays of the type described above generally are known as competitive binding assays. Since the binding entity frequently is a protein, the term competitive protein binding assays often is used.

The principles governing the use of such assays are, of course, well known. See, for example, A. Zettner, Clin. Chem., 19, 699 (1973) and A. Zettner and P. E. Duly, Clin. Chem., 20, 5 (1974). However, a brief discussion of such principles is useful at this point to aid in understanding the present invention.

In general, competitive binding assays involve three essential components: (1) the substance, or ligand, to be measured; (2) a labeled ligand; and (3) a binding agent which is specific for the ligand and labeled ligand. During the course of the assay, both the ligand and the labeled ligand complex, at least in part, with the binding agent. Thus, the labeled ligand typically is present in both free and complexed or bound states, with the quantity of bound labeled ligand being inversely related to the initial concentration of ligand. Consequently, the quantities to be measured are the amounts of either free or bound labeled ligand, or both. In order to measure such quantities, however, it is necessary to distinguish in some manner between free labeled ligand and bound labeled ligand.

In some cases, the nature of the label employed is significantly altered upon complexation of the labeled ligand with the binding agent. This makes it possible to measure the signal emitted by the label without further processing, e.g., without separating the free labeled ligand from the bound labeled ligand. Assays making use of this phenomenon generally are referred to as homogeneous assays, the best known of which perhaps are homogeneous enzyme immunoassays employing such enzymes as lysozyme, glucose-6-phosphate dehydrogenase, and malate dehydrogenase. For a review of the current status of quantitative enzyme immunoassays, see S. L. Scharpe et al., Clin. Chem., 22, 733 (1976). See also U.K. Patent Applications GB 2,018,424-A and GB 2,018,986-A which contain descriptions of homogeneous enzyme immunoassays and homogeneous fluorescence immunoassays.

It perhaps should be noted that homogeneous assays can involve heterogeneous systems, i.e., systems consisting of a liquid phase and a solid phase. See, for example, U.K. Patent Application GB 2,019,562-A and U.S. Pat. No. 3,853,987.

In many cases, however, it is necessary to physically separate the free labeled ligand from the bound labeled ligand, particularly where the label is a radioactive element. Separation procedures are, of course, well known and include, among others, electrophoresis; electrochromatography; gel filtration; starch gel electrophoresis; equilibrium dialysis; adsorption of free labeled ligand on solid adsorbents, such as charcoal, dextran-coated charcoal, protein-coated charcoal, silica, talc, ion-exchange resins, cellulose, and cross-linked dextrans; nonspecific precipitation of proteins, including protein-bound labeled-ligand complexes, by inorganic salts, such as ammonium sulfate and sodium sulfate, or by organic solvents, such as ethanol, methanol, acetone, and dioxane; immunoprecipitation; and the like.

Most of the foregoing separation procedures require a centrifugation step to facilitate separation of the insoluble phase from the supernatant. More importantly, however, the separation step per se may be, and often is, a significant source of error. In addition, many of the procedures are time consuming and ill suited for routine use in clinical laboratories.

Most of the above-mentioned disadvantages have been eliminated or minimized with the advent of solid-phase assays. As used herein, the term "solid-phase assay" means any assay in which an essential reagent is immobilized on an insoluble support or carrier whereby the immobilized reagent forms the basis for separating free labeled ligand from bound labeled ligand. As a practical matter, the immobilized reagent typically is the binding agent, e.g., antibody specific for the ligand and labeled ligand.

Although clearly possessing numerous advantages over other prior art procedures, solid-phase competitive binding assay protocols still require multiple centrifugation and/or decantation (aspiration) steps. Where permitted by the nature of the label employed, the method of the present invention eliminates the need to physically separate the solid phase from the supernatant, thereby eliminating the need for such multiple centrifugation and/or decantation (aspiration) steps.

SUMMARY OF THE INVENTION

It therefore is an object of the present invention to provide a method of measuring the degree of partitioning of a labeled species between free and bound states.

It also is an object of the present invention to eliminate the need to physically separate the solid phase from the supernatant in a solid-phase competitive binding assay where permitted by the nature of the label employed.

These and other objects will be apparent to those having ordinary skill in the art from a consideration of the specification and claims which follow.

Accordingly, the present invention provides a method of measuring the degree of partitioning of a labeled species between free and bound states which comprises the steps of:

A. incubating the labeled species in a liquid medium with an insoluble porous monolith having a means for binding a portion of the labeled species within the pores thereof, thereby partitioning the labeled species between free and bound states, which monolith is capable of substantially attenuating the signal emitted by the bound labeled species, wherein the liquid medium volume is sufficient to prevent the monolith from substantially attenuating the signal emitted by the free labeled species and the liquid medium per se does not substantially attenuate the signal emitted by the labeled species, whether free or bound; and B. measuring the composite signal emitted by the labeled species in both the free and bound states in the mixture of liquid medium and insoluble porous monolith, with the measured composite signal being directly related to the degree of partitioning of the labeled species between the free and bound states, wherein the difference between the attenuation of the signal emitted by the free labeled species and the attenuation of the signal emitted by the bound labeled species is at least about 40 percent when the attenuations of the signals emitted by the labeled species in the free and bound states are expressed as percentage values.

The method of the present invention is especially useful in a competitive binding assay for minute quantities of a physiologically- or medically-significant substance in a body fluid such as blood serum or plasma.

BRIEF DESCRIPTION OF THE DRAWINGS

FIG. 8 is a free thyroxine radioimmunoassay standard curve obtained by means of the present invention (see Example 9).

FIG. 9 illustrates the effect of interrupted agitation (shaking) on monolith binding kinetics, as described in Example 9.

FIG. 12 is a scatter diagram showing the correlation of TSH values determined by means of the present invention (Example 12) with the TSH values obtained by means of a commercially available radioimmunoassay kit.

DETAILED DESCRIPTION OF THE INVENTION

Figure 1:
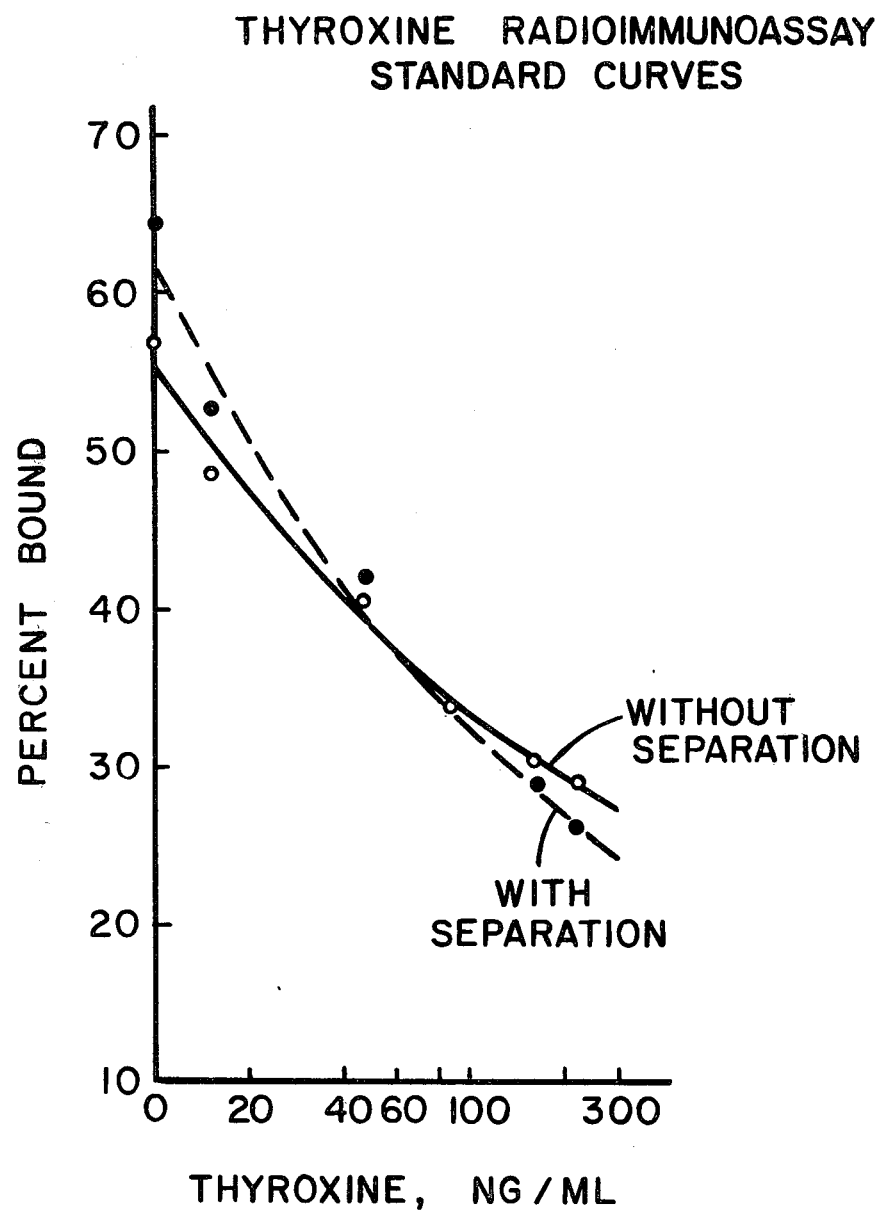
FIG. 1 is a comparison of total thyroxine radioimmunoassay standard curves obtained with and without separation of the monolith from the reaction mixture as described in Example 2.

As used herein, the terms "attenuating" and "attenuation" (and derivatives thereof) refer to the diminution of the signal emitted by the labeled species, but only as such signal is perceived by a signal sensing means. That is, such signal diminution is independent of the signal itself and occurs in the environment which is external to the labeled species. Thus, the terms "attenuating" and "attenuation" exclude processes whereby the strength or intensity of the signal emitted by the labeled species is diminished.

The first step in the method of the present invention comprises incubating the labeled species in a liquid medium with an insoluble porous monolith having a means for binding a portion of the labeled species within the pores thereof, thereby partitioning the labeled species between free and bound states, which monolith is capable of substantially attenuating the signal emitted by the bound labeled species, wherein the liquid medium volume is sufficient to prevent the monolith from substantially attenuating the signal emitted by the free labeled species and the liquid medium per se does not substantially attenuate the signal emitted by labeled species, whether free or bound.

The term "incubating" is used herein in its broadest sense to mean maintaining the labeled species and monolith in a liquid medium under conditions sufficient to partition the labeled species between free and bound states. Normally, such conditions will permit the system to reach, or at least closely approach, equilibrium. The attainment of equilibrium generally is not required, however, unless a very high degree of reproducibility is a concern.

The conditions required for such partitioning clearly are dependent upon such factors as the nature and quantity of the binding means, the nature and concentration of the labeled species, the nature and rate of the binding reaction or phenomenon, the size and shape of the monolith, the extent of porosity of the monolith, average pore diameter, incubation time, temperature, the presence or absence of agitation, and the like.

In view of the guidelines provided herein, however, the determination of suitable conditions for any given system can be determined readily by one having ordinary skill in the art. While several test runs may be necessary to optimize such conditions, undue experimentation is not required.

In general, the nature of the label moiety of the labeled species is not critical, provided that the signal emitted by the label is capable of being attenuated by the insoluble porous monolith. As a practical matter, the suitable labels can be classified as continuous signal emitters or triggered signal emitters. Continuous signal emitters typically are radioactive elements, such as $H^3$, $C^{14}$, $Na^{24}$, $P^{32}$, $S^{35}$, $K^{42}$, $Ca^{45}$, $Fe^{59}$, $Co^{57}$, $Co^{60}$, $I^{125}$, $I^{131}$, and the like. The nonmetallic isotopes are preferred in most instances, with $I^{125}$ and $I^{131}$ being most preferred, especially with a proteinaceous species.

Triggered signal emitters typically are fluorescent or chemiluminescent compounds. Examples of fluorescent compounds include, among others, acridine orange, 5-amino-2,3-dihydro-1,4-phthalazinedione, 7-amino-1,3-naphthalenedisulfonic acid, 4-amino-1-naphthalenesulfonic acid, p-anisaldehyde, chromotropic acid, coumarin, 2',7'-dichlorofluorescein, 6,7-dihydroxy-4-methylcoumarin, eosin, erythrosin, fluorescamine, fluorescein, 1-hydroxy-2-naphthoic acid, 3-hydroxy-2-naphthoic acid, trans-o-hydroxycinnamic acid, 4-methylumbelliferone, morin, 1-naphthol, 2-naphthol, 1-naphthol-3,6-disulfonic acid, 2-naphthol-6,8-disulfonic acid, 1-naphthol-2-sulfonic acid, 1-naphthol-4-sulfonic acid, 1-naphthol-6-sulfonic acid, 1-naphthylamine, o-phenylenediamine, p-phenylenediamine, phloxine B, resourfin, rhodamine, salicylic acid, 2',4',5',7'-tetrabromofluorescein, and the like. Examples of chemiluminescent compounds include, among others, 5-amino-2,3-dihydro-1,4-phthalazinedione (luminol), 5-amino-2,3-dihydro-6,7,8-trimethoxy-1,4-phthalazinedione, 2,4,5-triphenylimidazole, and the like.

The foregoing examples, of course, are given by way of illustration only and are not intended to limit either the spirit or the scope of the present invention. The use of any label which emits or can be made to emit a signal capable of being attenuated by the insoluble porous monolith is, in fact, contemplated by the present invention.

The use of labels such as those exemplified above, as well as others, is well known to those having ordinary skill in the art. Also well known are methods of incorporating such labels into a wide variety of species of interest.

With respect to such species, virtually any species can be employed, as long as the labeled species can be bound, at least in part, within the pores of the insoluble porous monolith. Because, as noted earlier, the method of the present invention finds its greatest application in clinical assays, species of interest typically include, by way of example only, hormones such as adrenocorticotropic hormone (ACTH), thyrotropic hormone (FSH), luteinizing hormone (LH), prolactin, growth hormone, oxytocin, vasopressin, calcitonin, insulin, glucagon, epinephrine, norepinephrine, estradiol, estrone, testosterone, dihydrotestosterone, progesterone, cortisol, aldosterone, corticosterone, thyroxine, 3,5,3'-triiodothyronine, and parathyroid hormone; vitamins such as Vitamin $B_{12}$ and folic acid; antibiotics such as penicillin; and the like.

As used herein, the term "monolith" generally is defined as an organized whole that acts as a single attenuating influence. As a practical matter, such monolith typically will consist of a single structure. Multiple independent structures can be employed, however, as long as the characteristics of the monolith as set forth herein are met. Thus, the term "monolith" as used herein clearly distinguishes the structures employed in the present invention from, for example, the particulate, relatively finely divided carriers or supports utilized in some prior art solid-phase competitive binding assays.

As already stated, the monolith must be porous. Because attenuation of the signal emitted by the labeled species must be independent of the signal itself, the substantial attenuation by the monolith of the signal emitted by bound labeled species in general can occur only when the monolith interfers with such signal in such a way as to substantially prevent such signal from reaching the signal sensing means. For such continuous and triggered signal emitters as described earlier, such interference arises because the monolith is substantially opaque to such signal. Accordingly, the monolith must be sufficiently porous to permit the bound labeled species to be located substantially within the monolith.

The degree and nature of such porosity, however, is not critical. Indeed, optimization of such variables as average pore diameter, pore diameter range, and monolith surface area, which are functions of porosity, as well as such variables as monolith shape and dimensions, must be determined on a case-by-case basis. Such optimization, though, can be determined readily by one having ordinary skill in the art without the need for undue experimentation.

The material of which the monolith is composed also is not critical, provided such material is capable of substantially attenuating the signal emitted by the bound labeled species. Thus, such material can be rigid, elastic, or even deformable, provided porosity characteristics are not significantly adversely affected. Further, such material can be inorganic or organic, or a combination of inorganic and organic materials. It should be apparent, however, that the choice of material is at least in part dependent upon the nature of the signal to be attenuated. Because the present invention is especially well suited for use in clinical assays, the monolith desirably will be a rigid, porous structure of closely controlled physical dimensions and material composition.

As a practical matter, the monolith composition and shape typically will be selected to give an attenuation of the signal emitted by the bound labeled species of at least about 50 percent. Preferably, such attenuation will be at least about 75 percent, and most preferably, at least about 90 percent.

For purposes of illustration only, assume that the label is a continuous emitter, e.g., a radioactive element emitting a gamma radiation. The monolith marterial and geometry, then, should be selected to provide substantial attenuation radiation emanating from the labeled species bound to the interior of the monolith. As discussed later, the monolith material and geometry also would be selected to accommodate the binding of an appropriate or desired amount of labeled species within the pores thereof. Suitable materials include, for example, bismuth, copper, iron and iron-containing alloys such as steel and stainless steel, gold, lead, molybdenum, nickel, platinum, silver, tantalum, tin, tungsten, zinc, mixtures of two or more of the foregoing, mixtures of one or more of the foregoing in an inorganic matrix, e.g., high-lead glass, mixtures of one or more of the foregoing in an organic matrix, and the like. Examples of suitable organic matrices include, among others, polyesters, such as poly(ethylene terephthalate); polyamides, such as nylon 6 and nylon 6.6; polyformaldehyde; poly(methyl) methacrylate); crosslinked polystyrene; polyisoprene; polychloroprene; polyethylene; and the like, to name but a few.

As a practical matter, especially suitable materials include stainless steel and nickel, primarily because porous structures of these materials are commercially available. Such structures typically are cylindrical or disc-shaped with a mean pore diameter of about $40\mu$ and a void volume of about 50 percent.

As already noted, the monolith must have a means for binding a portion of the labeled species within the pores thereof. Such means clearly is dependent, at least in part, on the monolith material and the labeled species to be bound.

In general, binding can be accomplished by physical or chemical bonding means, or both. Physical bonding, or physical adsorption, results from valence forces or such other attractive forces as van der Waals forces. The extent of such adsorption is greatly dependent upon the specific nature of the monolith material and the labeled species, as well as on temperature and the concentration of the labeled species.

Chemical bonding in general can vary from ionic to covalent bonding. Ionic bonding involves the attractive forces between oppositely charged ions and also includes such phenomenon as hydrogen or proton bonding. Covalent bonding, on the other hand, involves a sharing of electrons between two atoms. Covalent bonding tends to result in the strongest bonds and, for that reason, is more desired than other types of bonding.

Referring again to clinical competitive binding assays for purposes of illustration only, the binding means typically consists of antibodies specific for the substance of interest, which antibodies are covalently bound to the support or carrier. Thus, antibodies specific for the labeled species, which antibodies are covalently bound within the pores of the monolith, constitute an especially suitable binding means for use in the present invention.

More generally, however, suitable binding means for any given labeled species are known to those having ordinary skill in the art. Furthermore, the interrelationships among the labeled species, the monolith material, and the binding means are equally well known and understood by those having ordinary skill in the art.

In addition to the factors already discussed, the size, shape, degree or extent of porosity, and pore size of the monolith all affect the rate at which the labeled species diffuses into the monolith in order to be bound within the pores thereof. Moreover, manipulation of these factors to minimize diffusion times can adversely affect the ability of the monolith to attenuate the signal emitted by the labeled species which is bound within the pores thereof. For example, the shielding of gamma radiation is maximized by large structures, whereas diffusion times are minimized by small structures. In view of the above, there often must be a tradeoff or compromise between attenuation and diffusion such that a suitable level of overall performance is achieved.

The task of finding an appropriate compromise is rendered relatively simple if possible shape and size variations are considered on the basis of a constant structure volume. This can be done by beginning with the assumption that a certain porosity and internal surface area are required so that some minimum level of the requisite binding means is achieved. This leads to a total structure volume requirement. Alternative sizes and shapes then may be evaluated by scaling to that total volume requirement.

As a rule of thumb, diffusion times for a sphere, cylinder, and disc having equal structure volumes will be shortest for the disc and longest for the sphere; such shortest and longest diffusion times can differ by a factor of two or more. The required attenuation, however, is greatest for the sphere and least for the disc, although the two extremes tend to differ only by about ten percent or less. Thus, when the method of the present invention is to be used in an assay, such as a clinical assay, diffusion time probably becomes the more significant variable.

Diffusion time, of course, can be reduced significantly, regardless of the size, shape, and porosity characteristics of the monolith, by shaking, stirring, or otherwise agitating the liquid medium and monolith mixture. As a practical matter, such agitation is a necessity if the partitioning reaction is to be kept short enough for commercial utilization, such as in a clinical assay.

Because the monolith is porous, it follows that a portion of the liquid medium will occupy the monolith void volume. Consequently, the signal emitted by free labeled species contained in such void volume also will be significantly attenuated. In order to minimize overall attenuation of the signal emitted by free labeled species, the volume of the liquid medium must be significantly greater than the void volume of the monolith. For example, a liquid medium volume:void volume ratio of at least about 2 should limit the attenuation of the signal emitted by free labeled species to an acceptably low value, to about 50 percent. Obviously, larger ratios, e.g., about 5 or even about 10 or higher, would be desirable. Such larger ratios would be expected to give attenuation of the signal emitted by free labeled species of about 25 percent and about 10 percent, respectively.

Attenuation of the signal emitted by free labeled species in close proximity to, but not within the pores of, the monolith also can occur, depending upon the natue of the signal and the disposition of the monolith in relation to the liquid medium total volume. In general, such attenuation is minimized by employing a liquid medium volume which is significantly greater than the void volume of the monolith. Additionally, the disposition of the monolith in relation to the liquid medium volume is affected by the shape of the container. For example, a monolith centrally located in a liquid medium volume would produce a greater average attenuation of the signal emitted by free labeled species than if such monolith were noncentrally located. Thus, a partially filled test tube having the monolith in the bottom thereof would be a desirable arrangement to minimize such attenuation, assuming an appropriate liquid medium volume is employed.

The liquid medium per se must not substantially attenuate the signal emitted by the labeled species, whether free or bound. Otherwise, the nature of the liquid medium is not critical. As a practical matter, the liquid medium typically will be an aqueous solution. Depending upon the nature of the labeled species, however, nonaqueous systems can be employed.

The monolith, of course, must be substantially insoluble in the liquid medium. While absolute insolubility certainly is not required, the monolith must be sufficiently insoluble such that the binding means which is within the pores thereof remains intact. Because a number of suitable materials are available from which the monolith can be prepared, which materials are, for all practical purposes, essentially insoluble in the liquid medium, monolith insolubility rarely is an issue of concern. This is especially true where the liquid medium is aqueous in nature.

Incubation times and temperatures generally can be varied within a wide range. Incubation times typically will vary from about one to about 16 hours, although longer or shorter times may be desired. In general, incubation temperatures can range from the freezing point of the liquid medium to its boiling point. Practically, however, incubation temperatures will tend to be in the range of from about ambient temperature to about 40° C.

The second step of the method of the present invention comprises measuring the composite signal emitted by the labeled species in both the free and bound states in the mixture of liquid medium and insoluble porous monolith, with the measured composite signal being directly related to the degree of partioning of the labeled species between the free and bound states, wherein the difference between the attenuation of the signal emitted by the free labeled species and the attenuation of the signal emitted by the bound labeled species is at least about 40 percent when the attenuations of the signals emitted by the labeled species in the free and bound states are expressed as percentage values.

Ideally, the attenuation of the signal emitted by the free labeled species will be zero, while the attenuation of the signal emitted by the bound labeled species will be 100 percent. Under such a condition, the difference between the two obviously will be 100 percent.

Such a condition, however, is neither practical nor required. In order to more fully understand and appreciate the nature and extent of such difference, though, it will be helpful to develop a mathematical model for the method of the present invention.

As already stated, attenuation refers to the diminution of the signal emitted by the labeled species, but only as such signal is perceived by a signal sensing means. Thus, attenuation in percent can be expressed as follows:

$$A = 100(S_L/S_T) \quad (1)$$

where A represents attenuation in percent, $S_L$ represents the signal loss resulting from attenuation, and $S_T$ represents the total signal known to be present, i.e., the signal which would have been measured but for the attenuation. Equation (1), however, can be rewritten in terms of the measured signal, $S_M$:

$$A = 100(1 - S_M/S_T) \quad (2)$$

Upon rearranging equation (2), $$S_M = (1 - A/100)S_T \quad (3)$$

In the present invention, the measured signal consists of two components, one which is related to free labeled species and one which is related to bound labeled species. If $\alpha$ represents the attenuation of the former, expressed as percent, and $\beta$ represents the attenuation of the latter, also expressed as percent, and $S_{TF}$ and $S_{TB}$ are employed to represent the total signal known to be present in the free and bound states, respectively, equation (3) now can be used to represent the signal which is measured in the second step of the present invention. Thus, $$S_M = (1 - \alpha/100)S_{TF} + (1 - \beta/100)S_{TB} \quad (4)$$

A measurement made after a given incubation period would give a value for $S_M$ according to equation (4). If $\alpha$, $\beta$, and $S_T$ were known, equation (4) and the obvious relationship $S_T = S_{TF} + S_{TB}$ could be used to calculate $S_{TF}$ and $S_{TB}$. Results then could be reported in various ways, such as (a) bound-to-free ratio, $S_{TF}/S_{TB}$; (b) percent free, $100(S_{TF}/S_T)$; or (c) percent bound, $100(S_{TB}/S_T)$. Additionally, $\alpha$ and $\beta$ can be used to determine the conditions necessary to give a predetermined level of performance or to optimize one or more factors in a given procedure. Furthermore, $\alpha$ and $\beta$ can be used to assess the repeatability of attenuation levels (i.e., the constancy of $\alpha$ and $\beta$) for a series of measurements made pursuant to a given set of conditions. Although it is not possible to determine $\alpha$ and $\beta$ from a single measurement, they can be determined by the method described below.

Under ideal conditions (where $\alpha$ is 0 and $\beta$ is 100 percent), the measured signal, $S_M$, would be identical to the measured value for the signal emitted by the free labeled species when obtained by a conventional method employing a complete physical separation of free labeled species from bound labeled species. Under ideal conditions, then, the percent of free labeled species, F, and the percent of bound labeled species, B, can be represented by equations (5) and (6), respectively:

$$F = 100(S_{TF}/S_T) \quad (5)$$
$$B = 100(S_{TB}/S_T) = 100 - F \quad (6)$$

Similarly, equations (7) and (8) can be written for nonideal conditions:

$$F^* = 100(S_M/S_T) \quad (7)$$
$$B^* = 100 - F^* \quad (8)$$

which, under ideal conditions, reduce to equations (5) and (6), respectively.

Since $S_M$ is a function of $\alpha$ and $\beta$, $F^*$ and $B^*$ also are functions of $\alpha$ and $\beta$. When nonideal conditions exist, F, $F^*$, B, and $B^*$ can be related as follows:

$$B^* = 100 - 100(S_M/S_T) \quad (9)$$

$$= 100 - 100[(1 - \alpha/100)S_{TF} + (1 - \beta/100)S_{TB}]/S_T$$

Since $S_{TF} = S_T - S_{TB}$, $$\quad (10)$$

$$B^* = 100 - 100[(1 - \alpha/100)(S_T - S_{TB}) + (1 - \beta/100)S_{TB}]/S_T$$

$$= 100 - 100 - \alpha + 100(S_{TB}/S_T) - \alpha(S_{TB}/S_T) -$$

$$100(S_{TB}/S_T) + \beta(S_{TB}/S_T)$$

$$= (S_{TB}/S_T)(\beta - \alpha) + \alpha$$

Because $B = 100(S_{TB}/S_T)$, $$B^* = [(\beta - \alpha)/100]B + \alpha \quad (11)$$

Similarly, $$F^* = [(\beta - \alpha)/100]F + (100 - \beta) \quad (12)$$

To determine $\alpha$ and $\beta$, then, it is only necessary to determine both $B^*$ and B for each of two or more concentrations of labeled species in liquid medium. A plot of $B^*$ versus B on Cartesian coordinates yields a straight line having a slope and intercept equal to $(\beta - \alpha)/100$ and $\alpha$, respectively.

$B^*$, of course, is obtained by the method of the present invention using the measured composite signal, $S_M$, and equation (9). To obtain B, it is necessary to remove the monolith from the liquid medium after obtaining $B^*$. The monolith is washed thoroughly to remove liquid medium from the pores thereof. The washings are added to the liquid medium and the signal emitted by the free labeled species is measured. Because the measured signal now corresponds only to the signal emitted by free labeled species, B is readily calculated from the following equation:

$$B = 100(S_T - S_{TF})/S_T \qquad (13)$$

Equation (13), of course, is but another way of writing equation (6). By removing and washing the monolith, the net result is to make $\alpha$ equal to zero and $\beta$ equal to 100 percent.

The constancy of $\alpha$ and $\beta$ becomes important when the method of the present invention is used in a quantitative procedure, such as a clinical competitive binding assay. Consequently, it is useful to make a scatter plot of B* versus B for a suitably large number of measurements or samples. If $\alpha$ and $\beta$ are in fact highly repeatable or constant, no outlying data points will be present in the plot and a linear regression analysis will show a correlation coefficient near unity.

In view of the foregoing, it should be clear that the difference between the attenuation of the signal emitted by the free labeled species and the attenuation of the signal emitted by the bound labeled species refers to $\beta - \alpha$, and, as a minimum requirement, $\beta - \alpha$ must be at least about 40 percent. Preferably, $\beta - \alpha$ will be at least about 60 percent, and most preferably at least about 80 percent.

The means employed for measuring the composite signal emitted by the labeled species is dependent primarily on the nature of the signal. For any given signal, a variety of signal measuring means will be well known and understood by those having ordinary skill in the art.

The present invention is further illustrated by the examples which follow. Although all of the examples utilize radioactive isotopes as labels and some of the examples illustrate the adaptation of the method of the present invention to radioimmunoassays for hormones present in blood, the examples are not to be construed as in any way limiting the spirit and scope of the present invention. Unless otherwise stated, all temperatures are in degrees Celsius.

EXAMPLE 1

Preparation of Porous Cylindrical Monoliths Having Thyroxine Antibodies Immobilized Within the Pores Thereof The monoliths employed were stainless steel cylinders 4 mm in diameter and 8 mm in length (Centaur Chemical Company, Stamford, Conn.). The monoliths had a mean pore diameter of about 40$\mu$ and a void volume of about 50 percent. The monoliths had an average weight of 0.364 g, with a coefficient of variation of 2.1 percent (based on samples).

The monoliths were prepared for antibody coupling as follows. The monoliths were submerged in a ten percent solution (weight per volume) of $\gamma$-aminopropyltriethoxysilane (A-1100, Union Carbide Corporation, New York, N.Y.) in water at pH 3.45, under reduced pressure (water aspirator vacuum) to insure complete penetration of the solution into the pores of the monoliths. The mixture then was placed in a water bath at 75° for three hours. The monoliths were removed from the silane solution and washed with a volume of water equal to the volume of the silane solution. The monoliths then were dried overnight in an oven at 93°. The monoliths then were submerged in a 2.5 percent glutaraldehyde solution (prepared by diluting a 25 percent aqueous glutaraldehyde solution 1:10 with 0.1 M sodium phosphate buffer at pH 7.0) under reduced pressure (water aspirator vacuum) for three hours. The monoliths were removed from the glutaraldehyde solution and washed with 0.1 M sodium phosphate buffer at pH 7.9.

The treated monoliths were combined with 3.0 ml of a stock solution (prepared as described below) of an immunoglobulin-enriched fraction of an antithyroxine antiserum per 100 g of monoliths dissolved in sufficient 0.1 M phosphate buffer solution (PBS) at pH 7.0 to insure complete submersion of the monoliths (the 3.0 ml of stock solution was equivalent to 0.3 mg of protein per monolith). A water aspirator vacuum was applied to the resulting mixture for a time sufficient to insure complete penetration of the liquid phase into the pores of the monoliths. The mixture then was maintained at 4° on a reciprocating shake table (Eberbach Corporation, Ann Arbor, Mich.) for 48 hours. The monoliths were isolated, washed with 0.1 M pH 7.0 PBS, and stored wet at 4° in 0.1 M pH 7.0 PBS containing 0.12 percent (weight per volume) of bovine serum albumin (BSA).

The stock solution of an immunoglobulin-enriched fraction of an antithyroxine antiserum was prepared as follows. Rabbit antithyroxine antiserum was obtained from Corning Glass Works, Medical Products Division, Medfield, Mass. An immunoglobulin-enriched fraction was obtained from the antiserum through the differential precipitation of serum proteins by means of a neutral salt. Briefly, 60 ml of an aqueous saturated ammonium sulfate solution was added slowly with gentle agitation to 60 ml of antiserum which was maintained at pH 7.8. The resulting mixture was agitated slowly for five hours and then was centrifuged to collect the precipitated serum proteins. The precipitate was taken up in 60 ml of 0.03 M pH 8.0 PBS to give a solution containing 28 mg of serum proteins per ml of buffer. This solution was dialyzed against additional 0.03 M pH 8.0 PBS to remove residual ammonium sulfate. The resulting stock solution then was frozen until needed.

EVALUATION OF BINDING CONSTANTS

A measure of how strongly an antigen or hapten is bound to an antibody is given by the value of the equilibrium or binding constant which is defined as follows:

$$K = \frac{[Ag/Ab]}{[Ag][Ab]}$$

where K = the equilibrium or binding constant
[Ag/Ab] = the concentration of the antigen (or hapten)-antibody complex
[Ag] = the concentration of free or unbound antigen (or hapten)
[Ab] = the concentration of free or unbound antibody Clearly, the greater the value of K, the more strongly antigen is bound to antibody. If the bound and free antigen can be separated and the quantity bound measured, then the value of K can be determined by constructing a Scatchard plot; see, e.g., E. D. Day, "Advanced Immunochemistry", Williams & Wilkens Co., Baltimore, Md., 1972, pp. 118ff. Such a procedure is particularly suited to solid-phase immunoassay systems since the bound antigen is readily separated from the free or unbound antigen.

The value of K for the monolith-thyroxine antibody complex was determined as follows. Serial dilutions of a concentrated $I^{125}$-labeled thyroxine solution (Corning Glass Works, Medical Products Division, Medfield, Mass.) having a known thyroxine concentration were made and counted in a gamma counter (Packard Auto Gamma Scintillation Counter, Model 5220, Packard Instrument Company, Inc., Downers Grove, Ill.) to establish a suitable range of labeled thyroxine concentrations. The following protocol then was carried out twice, using total reaction volumes of 0.5 and 1.0 ml, respectively.

(1) A constant volume of each of five serial dilutions of the concentrated labeled thyroxine solution was pipetted into separate test tubes.

(2) To each tube was added a volume of 0.03 M pH 8.0 PBS containing 0.1 percent BSA and 1 mg/ml of 8-anilino-1-naphthalenesulfonic acid (ANS) sufficient to bring the total reaction volume to the desired level.

(3) Each tube was counted for one minute to obtain total counts.

(4) A monolith having thyroxine antibodies immobilized within the pores thereof, as described in Example 1, was added to each tube.

(5) Each reaction mixture thus obtained was incubated at ambient temperature overnight on a reciprocating shake table.

(6) The monolith then was removed from each tube and washed, with the washings being added to the liquid phase remaining in each tube.

(7) Each tube was counted for one minute to obtain the counts for free labeled thyroxine.

(8) The necessary calculations then were made.
  (a) Bound counts:
   Bound counts = Total counts - Free counts
  (b) Bound-to-free ratio, R:
   R = Bound counts/free counts
  (c) Bound thyroxine per ml, $BT_4$:
   $BT_4 = (Bound\ counts)(0.1\ ng/86,500\ counts)(1/Total\ reaction\ vol., ml)$
  (d) Binding constant, K:
   K = (Slope, ml/ng)($10^{-3}$ 1/ml)(770×$10^9$ ng/mole)
  (e) Binding sites per monolith, $BS_M$:
   $BS_M$ = (Intercept, ng/ml)(vol., ml)(mole/770×$10^9$ ng)(6.02×$10^{23}$ molecules/mole)(1 binding site/molecule)

The Scatchard plot data and calculations are summarized in Table 1.

TABLE 1

Summary of Scatchard Plot Data and Calculations for Thyroxine/Thyroxine Antibody System Using Stainless Steel Cylindrical Monoliths

| Total Reaction Volume, ml | Dilution | Total Counts[a] | Free Counts[a] | Bound Counts[a] | R | $BT_4$[b] |
|---|---|---|---|---|---|---|
| 0.5 | 1:20 | 26,542 | 6,664 | 19,878 | 2.98 | 0.046 |
|  | 1:10 | 50,362 | 13,001 | 37,361 | 2.87 | 0.086 |
|  | 1:5 | 102,062 | 30,957 | 71,105 | 2.30 | 0.164 |
|  | 1:2.5 | 203,015 | 82,834 | 120,181 | 1.45 | 0.278 |
|  | 1:1 | 492,933 | 327,137 | 165,796 | 0.51 | 0.383 |
| 1.0 | 1:20 | 27,266 | 8,497 | 18,769 | 2.21 | 0.022 |
|  | 1:10 | 50,168 | 17,565 | 32,603 | 1.86 | 0.038 |
|  | 1:5 | 102,281 | 39,339 | 62,942 | 1.58 | 0.073 |
|  | 1:2.5 | 200,170 | 88,682 | 111,488 | 1.26 | 0.129 |
|  | 1:1 | 503,610 | 323,452 | 180,158 | 0.56 | 0.208 |

[a] Counts per minute
[b] Bound thyroxine, ng/ml

Upon plotting the data thus obtained, essentially straight lines were obtained, as expected. The slopes of the two lines, representing the values of K for total reaction volumes of 0.5 and 1.0 ml, respectively, were 5.7×$10^9$ and 6.0×$10^9$ liters/mole, respectively. Additional calculations demonstrated that there were about 2×$10^{11}$ binding sites available per monolith.

EXAMPLE 2

Attenuation Effects of the Stainless Steel Cylindrical Monoliths

Using the standards and $I^{125}$-labeled thyroxine of the IMMO PHASE ® Thyroxine Radioimmunoassay Kit (Corning Glass Works, Medical Products Division, Medfield, Mass.), and the monolith-thyroxine antibody complexes of Example 1, the data necessary for the preparation of standard curves were obtained (a) without separation of the monolith from the reaction mixture before counting and (b) with separation and subsequent counting of the supernatant liquid only.

Each of a series of test tubes (two tubes per standard) was charged with 25 μl of standard, 100 μl of labeled thyroxine giving about 16,000 counts per minute (cpm), 350 μl of pH 8.0 PBS containing 0.1 percent BSA and 1 mg/ml of ANS and a single monolith-thyroxine antibody complex. Each reaction mixture was incubated at ambient temperature for 24 hours on a reciprocating shake table. Each tube then was counted in a gamma counter without separation of the monolith. The monolith was removed from each tube, carefully shaken to remove adhering solution, and discarded. The supernatant liquid remaining in each tube then was counted. The percent of labeled thyroxine bound within the pores the monolith was calculated in accordance with equations (9) and (13), supra. Where counts were obtained without separation, the calculated values correspond to B* [equation (9)]; where counts were obtained with separation, the calculated values correspond to B [equation (13)]. By plotting these calculated percent bound values versus thyroxine concentration in ng/ml, standard curves without separation and with separation, respectively, were obtained. These standard curves are shown in FIG. 1.

Figure 2:
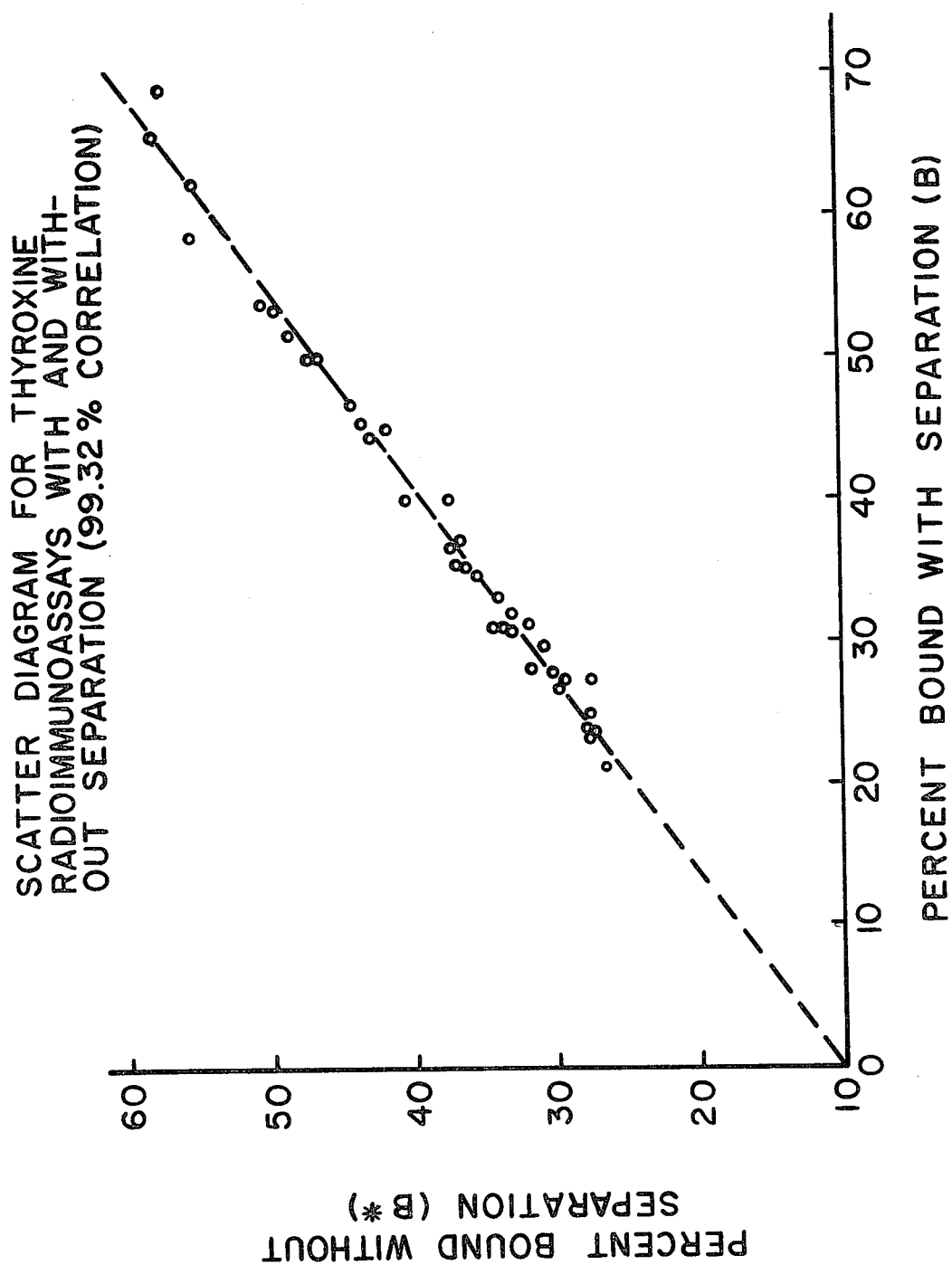
FIG. 2 is a scatter diagram showing the correlation of known total thyroxine concentrations determined with and without separation of the monolith from the reaction mixture, again as described in Example 2.

The procedure employed to generate the standard curve data then was repeated, using a series of standards and serum samples containing known concentrations of thyroxine. Again, the values for B and B* for each sample were calculated. This time, however, B was plotted versus B*. For accuracy, a computerized linear regression analysis was done to establish the correlation between B and B*. This plot of B versus B* and the calculated linear regression curve, which together constitute a scatter diagram, are shown in FIG. 2. According to the analysis, the correlation between B AND B* was 99.32 percent. The exceptionally high degree correlation shows that monolith-to-monolith attenuation effects are highly consistent and reproducible. Thus, the method of the present invention can be used as a replacement for the prior art separation procedures employed in solidphase clinical assays with no losses of accuracy or precision.

The above analysis also identified the values of the slope and intercept of the linear regression curve as 0.7215 and 10.26, respectively. The intercept, of course, is equal to $\alpha$. Because the slope equals $(\beta-\alpha)/100$ [see equation (11)], $\beta$ is readily calculated as being equal to 82.41. Thus, the stainless steel monoliths employed resulted in an attenuation of free labeled thyroxine of 10.26 percent and an attenuation of bound labeled thyroxine of 82.41 percent. Stated differently, the counts actually measured without separation, i.e., B*, were composed of the weighted sum of 89.74 percent of the true free counts and 17.59 percent of the true bound counts.

EXAMPLE 3

Attenuation Effects of Cylindrical Nickel Monoliths

The procedures of Example 2 were repeated, except that the stainless steel monolith-thyroxine antibody complexes were replaced with nickel monolith-thyroxine antibody complexes prepared in accordance with the procedure of Example 1. The nickel monoliths (Newmet Products, Terryville, Conn.) were cylindrical, 4 mm in diameter and 4 mm in length. The median pore diameter was in the 35–40$\mu$ range.

The correlation between B and B* with nickel monoliths 99.8 percent. The slope and intercept of the linear regression curve were 0.8570 and 5.45, respectively. Thus, $\alpha$ and $\beta$ were 5.45 and 91.15, respectively. Accordingly, the nickel monoliths resulted in an attenuation of free labeled thyroxine of 5.45 percent and an attenuation of bound labeled thyroxine of 91.15 percent. Alternatively, the counts actually measured without separation were composed of the weighted sum of 94.55 percent of the true free counts and 8.85 percent of the true bound counts.

EXAMPLE 4

Kinetic Studies Using Stainless Steel Cylindrical Monoliths

In order to determine diffusional and temperature effects relative to the use of the stainless steel monoliths of Examples 1 and 2, reaction kinetics studies were carried out with the monolith-thyroxine antibody complexes prepared in Example 1.

Such studies, readily accomplished because the measurements necessary to determine the degree of partitioning of the labeled species between free and bound states do not interrupt the partitioning process, involved four separate incubation conditions: (1) ambient temperature without shaking, (2) ambient temperature with shaking, (3) 37° without shaking, and (4) 37° with shaking. Four samples were run at each incubation condition and the results averaged. Again using the standards and I$^{125}$-labeled thyroxine of an IMMO PHASE ® Thyroxine Radioimmunoassay Kit, the following protocol was employed:

(1) To each test tube was added 25 $\mu$l of standard (i.e., 0.5 ng/ml of thyroxine), 350 $\mu$l of 0.03 M pH 8.0 PBS containing 0.1 percent BSA and 1 mg/ml of ANS, and 100 of labeled thyroxine solution.

(2) Each test tube was counted for one minute to obtain total counts.

(3) A monolith having thyroxine antibodies immobilized within the pores thereof (from Example 1) was added to each tube.

(4) Each tube was incubated under prescribed conditions and counted at hourly intervals for the first three to seven hours and again after from 23 to 27 hours (i.e., at equilibrium conditions).

In order to eliminate pore diffusion as a variable, the above protocol was repeated without shaking at 37°, except that the monolith was replaced with a nonporous support (commercially available 9 mm od × 12 mm high cylindrical nylon support having 10 2 mm × 12 mm fins radially configured and an activated, approximately 5-cm$^2$ surface suitable for the adsorption of antibodies) having thyroxine antibodies adsorbed thereon (prepared as described in Example 1, except that the $\gamma$-aminopropyltriethoxysilane and glutaraldehyde treatments were not employed), and the counting procedure of step (4) was carried out on the nonporous support after removal from the test tube.

The counts obtained during incubation were used to calculate B* in accordance with equation (9), except for the counts obtained with the nonporous support. Using the values of $\alpha$ and $\beta$ obtained in Example 2, a value of B corresponding to each value of B* was calculated by means of equation (11). Each value of B thus obtained represents the amount of labeled thyroxine actually bound within the pores of the monolith and also represents the value which would have been calculated if each count had been made after physically separating the monolith from the liquid phase. Thus, the counts obtained with the nonporous support were converted directly to B by means of equation (6). Each B value then was normalized by dividing it by the B value obtained at equilibrium and multiplying the resulting quotient by 100. Thus, $$B(\text{Normalized}) = 100(B_t/B_{Equilibrium})$$

Figure 3:
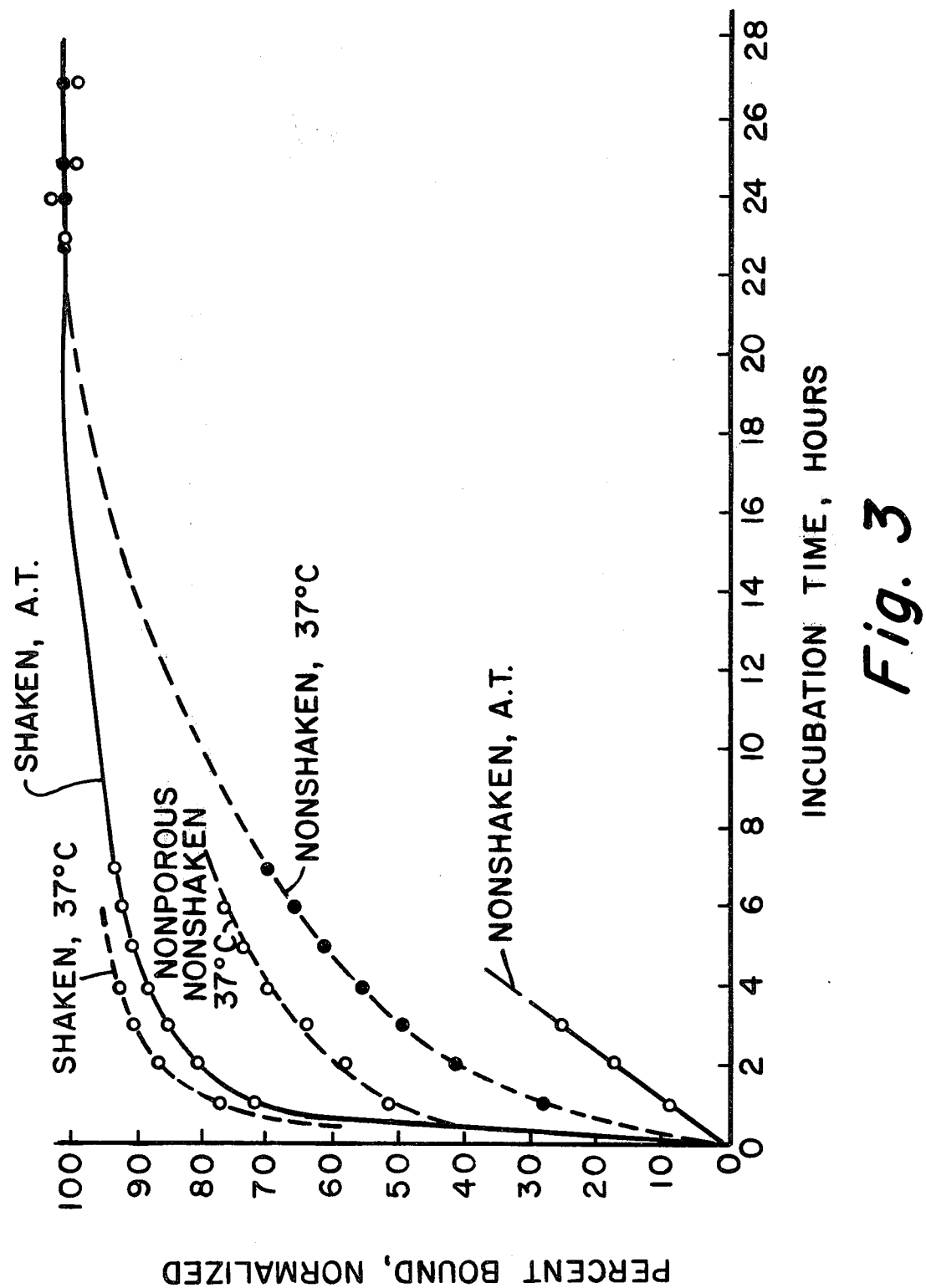
FIG. 3 illustrates diffusional effects associated with the use of the monolith at two different temperatures, as well as with and without agitation (see Example 4).

These normalized B values then were plotted versus incubation time, as shown in FIG. 3.

Kinetic data (not shown) also were obtained using a commercially available thyroxine radioimmunoassay kit : employing thyroxine antibodies adsorbed on the inner wall of a test tube (Clinical Assays, Cambridge, Mass.). The data obtained yielded results close to those obtained in the present example with a monolith under shaken, ambient temperature incubation conditions.

The effect of bulk diffusion, i.e., the diffusion of labeled thyroxine throughout the liquid medium, is seen by comparing curves based on shaken and nonshaken data. Thus, bulk diffusion effects are significant whether the reaction is carried out at 37° or ambient temperature.

A comparison of the curves based on ambient temperature data and data obtained at 37° demonstrate the effect of incubation temperature. Not unexpectedly, increasing the incubation temperature increased the kinetics of the reaction.

This effect was significant without shaking, but minor with shaking. Since shaking obviously is desired incubation temperature is of minor importance as long as deleterious effects are avoided.

Finally, the effect of pore diffusion, i.e., diffusion of labeled thyroxine into and within the monolith, is seen by comparing the curves obtained from the nonporous support data and the nonshaken 37° data. Pore diffusion obviously is significant, but less so than bulk diffusion.

As long as shaking (or other suitable means of agitation) is employed, incubation times of about 2 to about 4 hours are reasonable with the stainless steel monoliths employed.

EXAMPLE 5

Total Thyroxine Radioimmunoassay

A total thyroxine radioimmunoassay was carried out on 19 serum samples on two different days, which required the preparation of a standard curve for each day. The stainless steel monolith-thyroxine antibody complexes of Example 1 were used.

The assay protocol employed was the standard curve procedure of Example 2, except that a 2.5-hour incubation period was used on the first day and a 3.5-hour incubation period was used the second day. All standards were done in triplicate. The serum samples were done in triplicate on the first day and in duplicate on the second day. Four serum samples were common to both days, but were treated as different and distinct samples for statistical purposes. Because of poor pipetting precision, the contents of each test tube were counted after adding the PBS, labeled thyroxine, and 25 $\mu l$ of standard or serum sample to obtain a total value for that tube.

In each case, B* was calculated as described in Example 2 [i.e., from equation (9)]. A standard curve was prepared for each day by plotting the average B* value per standard versus the thyroxine concentration of that standard (in ng/ml). The thyroxine concentration for each serum sample run that day then was determined from the standard curve on the basis of the average B* value for each sample.

Each serum sample also was assayed for total thyroxine by means of the IMMO PHASE ® Thyroxine Radioimmunoassay Kit in accordance with the manufacturer's instructions. For the purposes of this example, the values thus obtained were presumed to be the correct or true values.

The data thus obtained for samples run on each day are summarized in Tables 2 and 3 below.

TABLE 2

Total Thyroxine Radioimmunoassay
Summary of First Day's Data

| | | Thyroxine, ng/ml | |
|---|---|---|---|
| Sample | B* | True Value | Observed |
| V-1 | 37.7 | 23.4 | 32 |
| V-2 | 43.1 | 26.5 | 22 |
| V-18 | 31.9 | 86 | 82 |
| V-20 | 31.1 | 86 | 88 |
| V-23 | 27.4 | 172 | 162 |
| V-27 | 24.5 | 156 | 260* |

*Questionable result

TABLE 3

Total Thyroxine Radioimmunoassay
Summary of Second Day's Data

| | | Thyroxine, ng/ml | |
|---|---|---|---|
| Sample | B* | True Value | Observed |
| V-1 | 35.4 | 23.4 | 52 |
| V-2 | 38.0 | 26.5 | 38 |
| V-3 | 35.2 | 49.0 | 53 |
| V-5 | 40.0 | 50.6 | 30.5 |
| V-6 | 30.4 | 80 | 100 |
| V-7 | 34.6 | 78 | 58 |
| V-9 | 37.8 | 45 | 40 |

TABLE 3-continued

Total Thyroxine Radioimmunoassay
Summary of Second Day's Data

| | | Thyroxine, ng/ml | |
|---|---|---|---|
| Sample | B* | True Value | Observed |
| V-12 | 34.2 | 74 | 68 |
| V-13 | 28.8 | 100 | 126 |
| V-17 | 28.2 | 117 | 138 |
| V-19 | 30.4 | 100 | 100 |
| V-23 | 26.3 | 172 | 190 |
| V-24 | 29.9 | 117 | 106 |
| V-27 | 26.2 | 156 | 195 |

Figure 4:
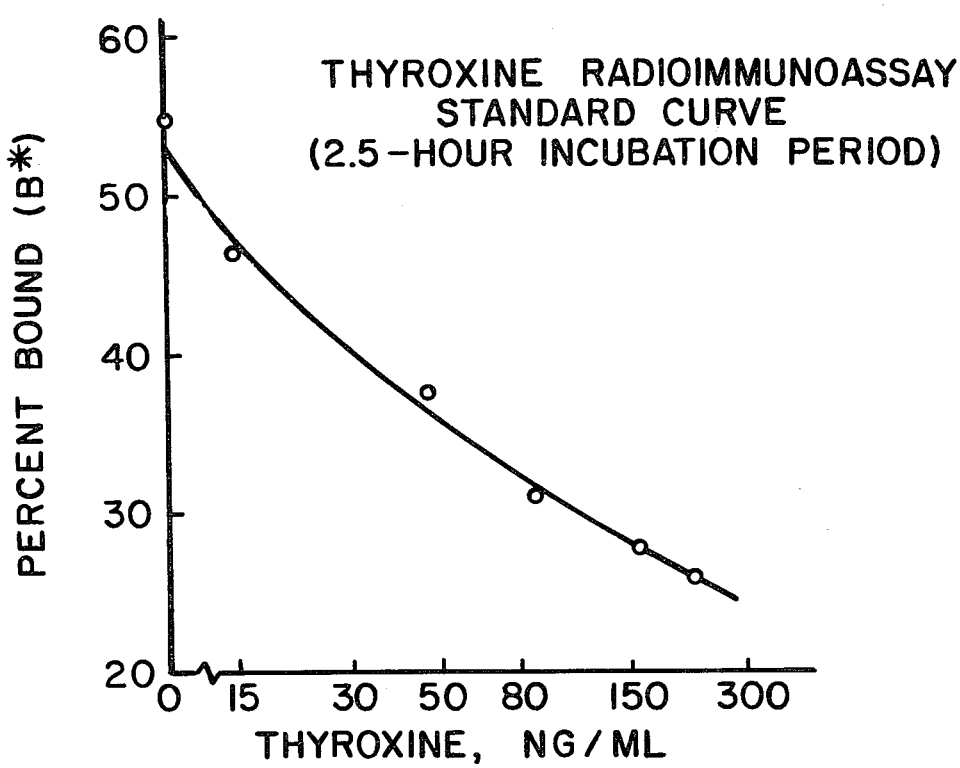
FIG. 4 is a first total thyroxine radioimmunoassay standard curve, obtained by means of the present invention with a 2.5-hour incubation period (see Example 5).
Figure 5:
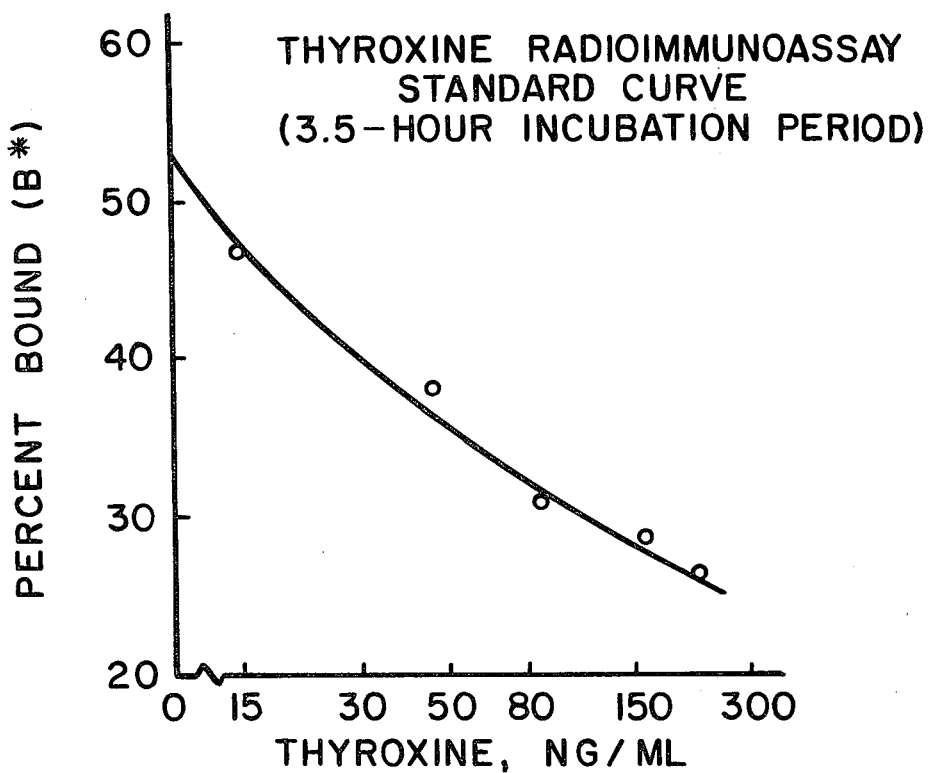
FIG. 5 is a second total thyroxine radioimmunoassay standard curve, obtained by means of the present invention with a 3.5-hour incubation period (see Example 5).

FIGS. 4 and 5 show the standard curves for each day, respectively. The two standard curves are almost identical, although the longer incubation period on the second day caused an average increase of 2.7 percent in the standard B* values.

Although not shown in either the data or the figures, the coefficient of variation for duplicate runs was estimated to be about 8 percent.

Figure 6:
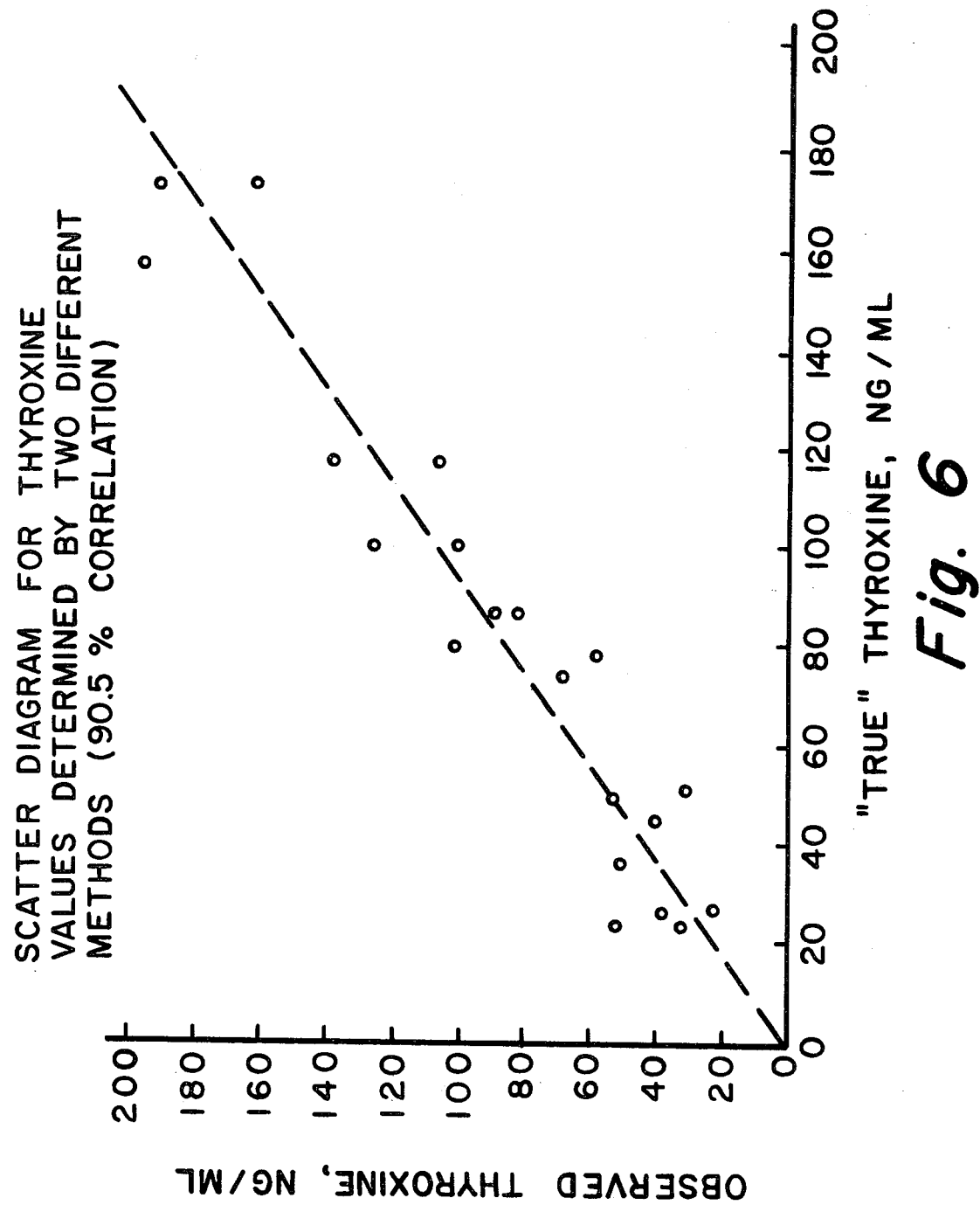
FIG. 6 is a scatter diagram showing the correlation of total thyroxine values determined by means of the present invention (Example 5) with the total thyroxine values obtained by means of a commercially available radioimmunoassay kit.

Finally, the observed thyroxine concentration values were compared with the true values by means of a computerized linear regression analysis as described in Example 2. The resulting scatter diagram is shown in FIG. 6. The slope and intercept of the linear regression curve were calculated to be 1.060 and 0.14, respectively, indicating that the two procedures tend to give the same result. The correlation coefficient was found to be 90.5 percent, an especially good result in view of the fact that no attempts were made to optimize the use of the method of the present invention.

EXAMPLE 6

Preparation of Porous Disc-Shaped Monoliths Having Thyroxine Antibodies Immobilized Within the Pores Thereof The procedure of Example 1 was repeated, except that the cylindrical monoliths were replaced with 316 stainless steel discs 8 mm in diameter and 1.6 mm in thickness and the amount of protein per monolith was increased to 0.5 mg. Mean pore diameters were about $40\mu$ and the total surface area of each disc was about 60 cm$^2$. In a random sampling of 10 discs, the average weight per disc was 0.330 g with a coefficient of variation of 0.3 percent. The discs were obtained as Stock No. S-2298 from Sintered Specialties, Janesville, Wisc.

The Scatchard plot data were obtained using a total liquid volume of 0.5 ml per tube and serial dilutions of $I^{125}$-labeled thyroxine from about 500,000 cpm to about 25,000 cpm. The data obtained are summarized in Table 4.

TABLE 4

Summary of Scatchard Plot Data and Calculations for
Thyroxine/Thyroxine Antibody System Using
Stainless Steel Disc-Shaped Monoliths

| Total Reaction Volume, ml | Dilution | R | BT$_4$ |
|---|---|---|---|
| 0.5 | 1:20 | 1.63 | 0.035 |
| | 1:10 | 1.66 | 0.070 |
| | 1:5 | 1.44 | 0.122 |
| | 1:2.5 | 1.40 | 0.238 |
| | 1:1 | 0.96 | 0.497 |

Upon plotting the data, the value of K was determined to be $1 \times 10^9$ liters/mole. The number of binding sites available per disc were calculated to be about $5 \times 10^{11}$.

EXAMPLE 7

Attenuation Effects of the Disc-Shaped Monoliths

In conjunction with the data-collecting procedure of Example 6, the procedure of Example 2 also was employed in order to evaluate the attenuation effects of the disc-shaped monoliths.

The scatter diagram thus obtained showed a correlation between B and B* of 99.29 percent. In addition, $\alpha$ was found to be 6.2 percent and $\beta$ was 91.5 percent. Accordingly, the counts actually measured without separation were composed of the weighted sum of 93.8 percent of the true free counts and 8.5 percent of the true bound counts.

Upon comparing these results with those of Example 2, it is seen that where the label is $I^{125}$, the disc configuration is a more effective attenuator than the cylindrical configuration.

EXAMPLE 8

Kinetic Studies Using the Disc-Shaped Monoliths

The procedure of Example 4 was repeated, except that the stainless steel cylindrical monoliths were replaced with the stainless steel disc-shaped monoliths of Example 6 and incubation was carried out with shaking at ambient temperature only. The results are shown in FIG. 7 which, for comparative purposes, includes the corresponding curve from FIG. 3 for the stainless steel cylindrical monoliths.

Figure 7:
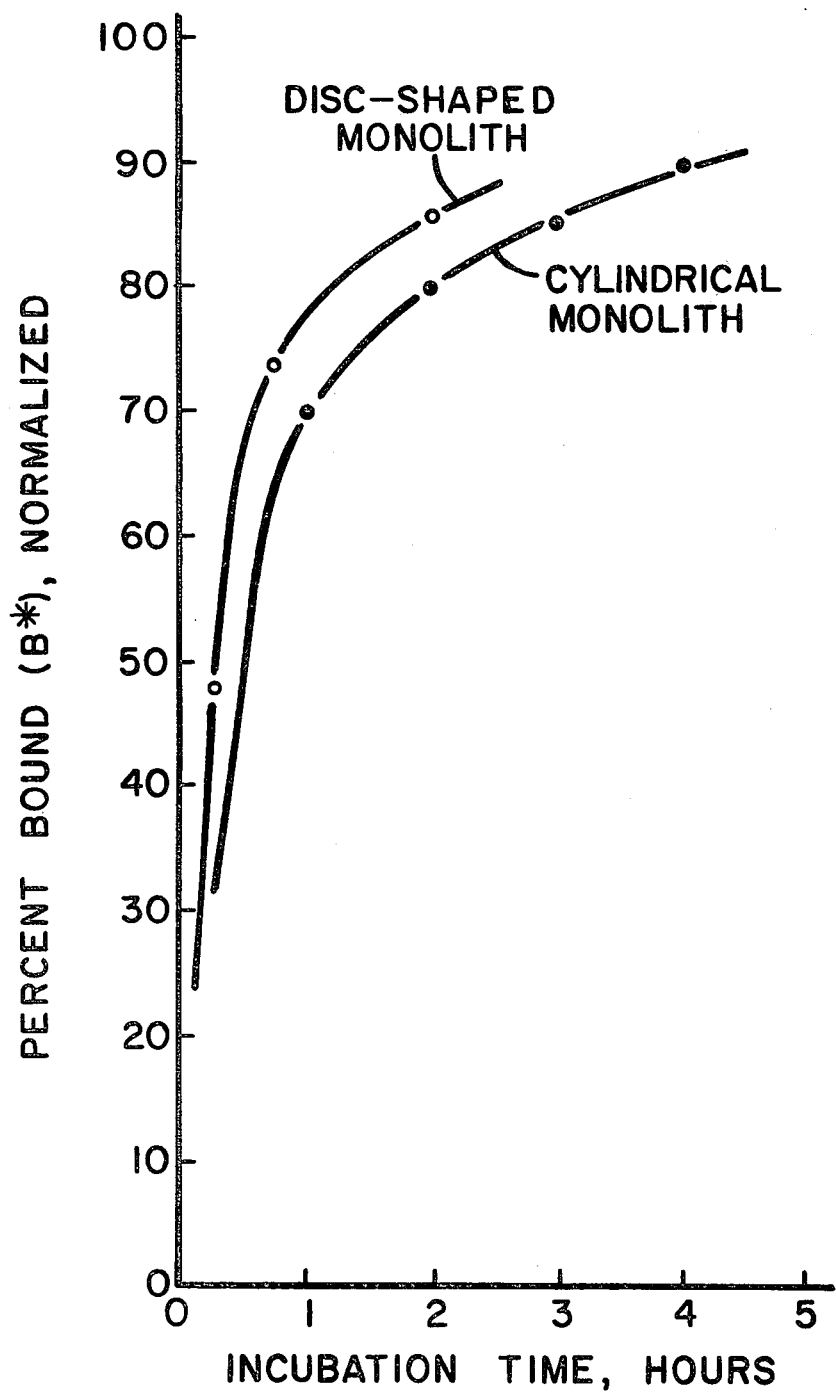
FIG. 7 compares the competitive binding kinetics of two different monolith shapes in a total thyroxine competitive binding assay (see Example 8).

From FIG. 7, it is seen that the disc-shaped monolith is preferred over the cylindrical monolith under the conditions employed. For example, the partitioning reaction was 85 percent complete with the cylindrical monolith in three hours, whereas with the disc-shaped monolith only two hours were required to reach the same point. Thus, it should be apparent that optimum monolith shapes can be defined readily by those having ordinary skill in the art.

EXAMPLE 9

Free Thyroxine Standard Curve

Using the standards and $I^{125}$-labeled thyroxine of the IMMO PHASE® Thyroxine Radioimmunoassay Kit and the disc-shaped monolith-thyroxine antibody complexes of Example 6, the data necessary for the preparation of a free thyroxine were obtained as described below, using five standards covering free thyroxine concentrations from 0.3 to 6.0 ng/dl (each standard was run in triplicate and averaged).

The following protocol was employed:
(1) To each test tube at ambient temperature was added 25 $\mu$l of the standard and 450 $\mu$l of 0.03 M pH 8.0 PBS containing 0.1 percent BSA.
(2) Each tube was allowed to stand 15 minutes.
(3) To each tube was added a stainless steel disc-shaped monolith having thyroxine antibodies immobilized within the pores thereof (from Example 6).
(4) Each tube was incubated for 20 minutes at ambient temperature on a reciprocating shake table.
(5) The liquid phase was aspirated from each test tube.
(6) One ml of the PBS was added to each test tube as a wash and aspirated.
(7) To each tube was added 500 $\mu$l of 0.03 M pH 8.0 PBS containing 0.1 percent BSA, 100 $\mu$g ANS, and an amount of labeled thyroxine solution sufficient to provide a total count rate of 65,000 counts per minute.
(8) Each tube was incubated for 30 minutes at ambient temperature on a reciprocating shake table.
(9) Each tube then was counted on a gamma counter (without removing the monolith).
(10) A value for total counts was obtained by counting four 500-$\mu$l aliquots of the PBS added in step (7) and taking the average thereof.

B* was calculated by means of equation (9) and plotted versus free thyroxine concentration to give a free thyroxine standard curve, shown in FIG. 8.

From Examples 4 and 8, it is obvious that nonequilium conditions exist at the end of the incubation periods typically employed in the examples. Consequently, the above-described measurements were monitored by recounting the 6.0 ng/dl standard tubes at hourly intervals after removal from the shake table. B* was calculated for these new measurements as described above and was found to increase by only about one percent over a three-hour nonshaken interval. Upon resuming shaking for a one-hour period, B* was found to increase as though shaking had not been interrupted. This phenomenon is illustrated in FIG. 9.

From FIG. 9, it is apparent that measurements can be made under nonequilibrium conditions, which conditions then can be preserved for reasonable periods of time by simply ceasing agitation.

Although the protocol employed in this example was not optimized for a free thyroxine assay, it was observed that exclusion of the BSA from all buffers improved the repeatability of the data.

EXAMPLE 10

Preparation of Porous Cylindrical Monoliths Having Thyroid Stimulating Hormone (TSH) Antibodies Immobilized Within the Pores Thereof The stainless steel disc-shaped monoliths of Example 6 were prepared for coupling as described in Example 1. Rabbit anti-TSH antiserum, obtained from Corning Glass Works, Medical Products Division, was processed as described in Example 1 for the thyroxine antiserum. The coupling reaction also was carried out as described in Example 1, except that the amount of protein per monolith was increased to 0.5 mg and the concentration of BSA in the storage buffer was increased to 2.5 percent.

Using five TSH standards covering a TSH concentration range of from 0 to 60 $\mu$IU/ml (Corning Glass Works, Medical Products Division) and $I^{125}$-labeled TSH from a Beckman RIA PHASE H TSH Radioimmunoassay Kit (Beckman Instruments, Inc., Fullerton, Calif.), the following protocol was carried out to verify the presence of TSH antibodies within the pores of the monoliths, each standard being run in duplicate:
(1) To each test tube was added 200 $\mu$l of labeled TSH solution, 300 $\mu$l of standard, and one of the above monoliths having TSH antibodies immobilized within the pores thereof.
(2) Each tube was incubated overnight at ambient temperature on a reciprocating shake table.
(3) Each tube was counted hourly for the first three hours and again at the end of the overnight incubation period.
(4) Total counts were obtained by averaging the counts obtained from four 200-$\mu$l aliquots of labeled TSH solution.

Figure 10:
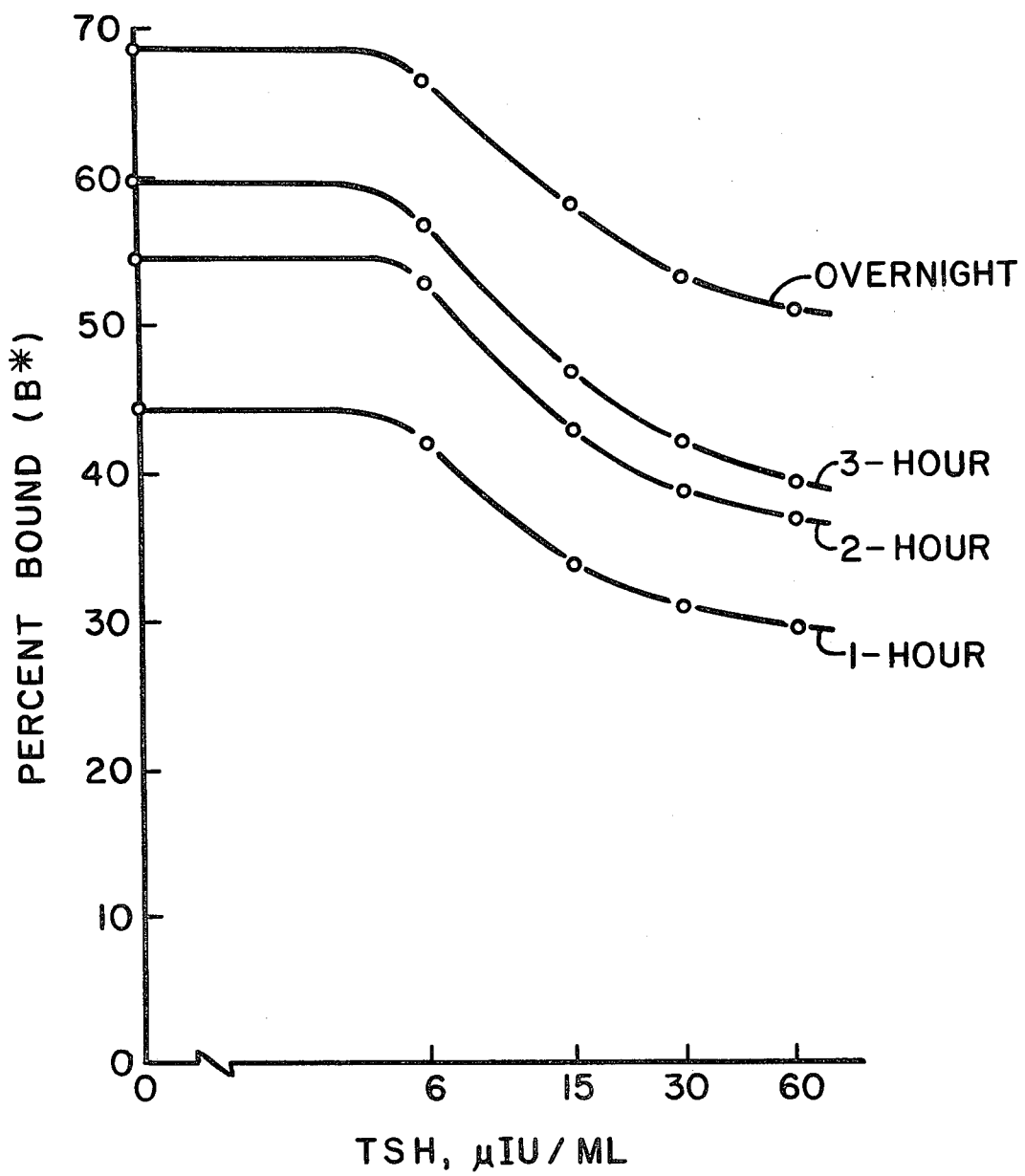
FIG. 10 consists of four thyroid stimulating hormone (TSH) radioimmunoassay standard curves obtained by means of the present invention with four different incubation periods, as described in Example 10.

B* then was calculated by means of equation (9). The calculated B* values for the several incubation periods then were plotted versus TSH concentration, giving four separate curves as shown in FIG. 10.

It is apparent that TSH antibodies were present within the pores of the monoliths. Also, the TSH reaction kinetics were slower than the thyroxine reaction kinetics, a result which perhaps is not unexpected in view of the large difference between the molecular weights of TSH and thyroxine (25,000 and 770, respectively).

EXAMPLE 11

TSH Standard Curve

Using seven TSH standards (run in duplicate) covering a TSH concentration range of from 0 to 60 µIU/ml and $I^{125}$-labeled TSH from an IMMO PHASE ® TSH Radioimmunossay Kit, the disc-shaped monolith-TSH antibody complexes of Example 10 were employed in the following reverse sandwich protocol to generate data for a TSH standard curve:

(1) To each test tube was added 125 µl of standard and 125 µl of labeled TSH solution.
(2) Each tube was counted to obtain total counts.
(3) Each tube was incubated for two hours at ambient temperature.
(4) To each tube was added 250 µl of 0.05 M pH 7.4 PBS which was 0.15 M in sodium chloride and which contained 2.5 percent BSA, and a disc-shaped monolith-TSH antibody complex of Example 10.
(5) Each tube was incubated overnight at ambient temperature on a reciprocating shake table.
(6) Each tube was counted after an initial three-hour period and again at the end of the overnight incubation.

Figure 11:
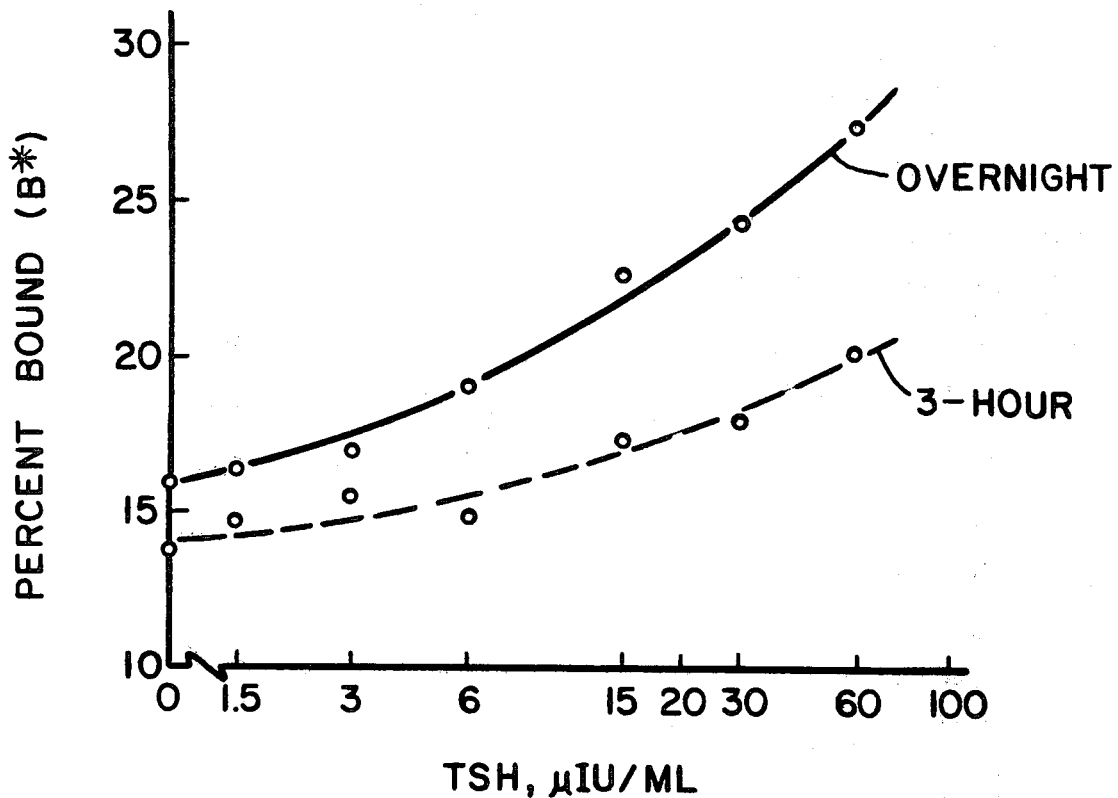
FIG. 11 consists of two thyroid stimulating hormone reverse sandwich radioimmunoassay standard curves obtained by means of the present invention with two different incubation periods, as described in Example 11.

B* was calculated from each measurement in accordance with equation (9). The resulting B* values were plotted versus TSH concentration to give two standard curves, one for a three-hour incubation period and one for an overnight incubation period, as shown in FIG. 11.

Of the two incubation periods, overnight incubation clearly resulted in the more sensitive standard curve. Although the displacement of this more sensitive curve is not great (11.5 percent), it compares favorably with that of the standard curve obtained with a commercially available kit (11.1 percent, IMMO PHASE ® TSH Radioimmunoassay Kit, data not shown). As used herein, the term "displacement" means the difference between the B* value at a TSH concentration of 60 µIU/ml and that at a TSH concentration of 0.

EXAMPLE 12

TSH Radioimmnoassay

The procedure of Example 11 was repeated with the same seven standards and labeled TSH solution, plus 15 serum samples as unknown, except that the volumes of standard or sample and labeled TSH solution were reduced from 125 µl to 100 µl each and the volume of PBS was increased from 250 µl to 300 µl. Standards and serum samples were run in duplicate and a single overnight incubation period (about 15 hours) was employed. The sample measurements thus obtained were converted to B* values as in Example 11. The B* values, in turn, were converted to TSH concentrations by means of a standard curve (not shown).

Separate TSH determinations for the 15 serum samples were made with the IMMO PHASE ® TSH Radioimmunoassay Kit in accordance with the manufacturer's instructions. For the purposes of this example, the values thus obtained were presumed to be the correct or true values.

The data obtained are summarized in Table 5.

TABLE 5

TSH Radioimmunoassay Summary

| | | TSH, µIU/ml | |
|---|---|---|---|
| Sample | B* | True Value | Observed |
| 1 | 17.9 | 2.0 | 2.6 |
| 3x | 17.5 | 2.4 | 2.2 |
| 4 | 18.3 | 4.1 | 3.2 |
| 10 | 19.8 | 6.6 | 5.8 |
| 11 | 18.8 | 9.3 | 3.9 |
| 12 | 20.2 | 11.5 | 6.7 |
| 3 | 22.8 | 12.6 | 16.0 |
| 15 | 22.9 | 14.3 | 16.0 |
| 16 | 23.1 | 18.7 | 17.2 |
| 14 | 22.2 | 14.1 | 13.3 |
| 27 | 25.0 | 29.7 | 28.0 |
| 29 | 26.3 | 45.5 | 37.5 |
| 30 | 26.7 | 46.8 | 41.0 |
| 31 | 29.2 | 56.5 | 67.0 |
| 32 | 29.0 | 60.9 | 65.0 |

As in Example 2, a computerized linear regression analysis was carried out to establish the correlation between the observed TSH concentration and the "true" value. The scatter diagram thus obtained is shown in FIG. 12. According to the analysis, the correlation between the two values was 95.8 percent. The slope and intercept of the linear regression curve were calculated to be 1.050 and $-1.75$ µIU/ml, respectively. Consequently, there is good agreement between the two methods which suggests that the method of the present invention can be employed in conventional TSH radioimmunoassays.

As already indicated, it is to be understood that the foregoing detailed description is given merely by way of illustration and that many variations may be made therein without departing from the spirit and scope of the invention. In fact, the scope of the present invention is limited only by the ability of one having ordinary skill in the art to determine monolith composition and characteristics for a given label and the means of binding a portion of a given labeled species within the pores of the monolith.

For example, U.S. Pat. No. 3,886,080 teaches a method of binding or coupling chelating agents to inorganic ; carriers or supports. Thus, by combining such teaching with the method of the present invention, it is possible to measure the degree of partitioning of labeled polyvalent metal ions between free and bound states. Other variations, of course, will be apparent to those having ordinary skill in the art.

We claim:

1. A method of measuring the degree of partitioning of a labeled species between free and bound states which comprise the steps of:
   A. incubating the labeled species in a liquid medium with an insoluble porous monolith having a means for binding a portion of the labeled species within the pores thereof, thereby partitioning the labeled species between free and bound states, which monolith is capable of substantially attenuating the signal emitted by the bound labeled species, wherein the liquid medium volume is sufficient to prevent the monolith from substantially attenuating the signal emmitted by the free labeled species and the liquid medium per se does not substantially attenuate the signal emitted by labeled species, whether free or bound; and B. measuring the composite signal emitted by the labeled species in both the free and bound states in the mixture of liquid medium and insoluble porous monolith, with the measured composite signal being directly related to the degree of partitioning of the labeled species between the free and bound states, wherein the difference between the attenuation of the signal emitted by the free labeled species and the attenuation of the signal emitted by the bound labeled species is at least about 40 percent when the attenuations of the signals emitted by the labeled species in the free and bound states are expressed as percentage values;

wherein the insoluble porous monolith is composed essentially of iron, stainless steel, nickel, lead, or high-lead glass.

2. The method of claim 1 in which the difference between the attenuation of the signal emitted by the free labeled species and the attenuation of the signal emitted by the bound labeled species is at least about 60 percent.

3. The method of claim 2 in which the difference between the attenuation of the signal emitted by the free labeled species and the attenuation of the signal emitted by the bound labeled species is at least about 80 percent.

4. The method of claim 1 in which the liquid medium volume is sufficient to give an attenuation of the signal emitted by the free labeled species of no more than about 50 percent.

5. The method of claim 4 in which the liquid medium volume is sufficient to give an attenuation of the signal emitted by the free labeled species of no more than about 25 percent.

6. The method of claim 5 in which the liquid medium volume is sufficient to give an attenuation of the signal emitted by the free labeled species of no more than about 10 percent.

7. The method of claim 1 in which the label of the labeled species is a continuous signal emitter.

8. The method of claim 7 in which the label of the labeled species is a radioactive element.

9. The method of claim 8 in which the radioactive element is iodine.

10. The method of claim 9 in which the radioactive element is $I^{125}$.

11. The method of claim 1 in which the label of the labeled species is a triggered signal emitter.

12. The method of claim 11 in which the label of the labeled species is a chemiluminescent moiety.

13. The method of claim 11 in which the label of the labeled species is a fluorescent moiety.

14. An insoluble porous monolith having a means for binding a portion of a labeled species within the pores thereof, which monolith has a composition and shape selected to give an attenuation of the signal emitted by labeled species subsequently bound within the pores thereof of at least about 50 percent, which insoluble porous monolith is composed essentially of iron, stainless steel, nickel, lead, or high-lead glass.

15. The monolith of claim 14 in which the monolith has a composition and shape selected to give an attenuation of the signal emitted by labeled species subsequently bound within the pores thereof of at least about 75 percent.

16. The monolith of claim 15 in which the monolith has a composition and shape selected to give an attenuation of the signal emitted by labeled species subsequently bound within the pores thereof of at least about 90 percent.

* * * * *